(12) United States Patent
Suwanakitti et al.

(10) Patent No.: US 10,011,842 B2
(45) Date of Patent: Jul. 3, 2018

(54) ESCHERICHIA COLI CELL LINE WITH THYA KNOCKOUT, FOLA KNOCKOUT, AND ONE OR BOTH OF FOLP KNOCKOUT, AND FOLK KNOCKOUT

(71) Applicant: National Science And Technology Development Agency, Pathumthani (TH)

(72) Inventors: Nattida Suwanakitti, Pathumthani (TH); Yuwadee Talawanich, Pathumthani (TH); Yongyuth Yuthavong, Pathumthani (TH); Sumalee Kamchonwongpaisan, Pathumthani (TH)

(73) Assignee: National Science and Technology Development Agency, Pathumthani (TH)

( * ) Notice: Subject to any disclaimer, the term of this patent is extended or adjusted under 35 U.S.C. 154(b) by 9 days.

(21) Appl. No.: 15/025,881

(22) PCT Filed: Sep. 18, 2014

(86) PCT No.: PCT/TH2014/000045
§ 371 (c)(1),
(2) Date: Mar. 29, 2016

(87) PCT Pub. No.: WO2015/047199
PCT Pub. Date: Apr. 2, 2015

(65) Prior Publication Data
US 2016/0230178 A1 Aug. 11, 2016

(30) Foreign Application Priority Data
Sep. 30, 2013 (TH) .............................. 1301005569

(51) Int. Cl.
| | |
|---|---|
| *C12P 17/08* | (2006.01) |
| *C12N 15/70* | (2006.01) |
| *C12N 9/06* | (2006.01) |
| *C12N 9/10* | (2006.01) |
| *C12N 9/12* | (2006.01) |
| *C12N 9/00* | (2006.01) |
| *C12Q 1/48* | (2006.01) |

(52) U.S. Cl.
CPC ............ *C12N 15/70* (2013.01); *C12N 9/003* (2013.01); *C12N 9/1007* (2013.01); *C12N 9/1085* (2013.01); *C12N 9/1235* (2013.01); *C12N 9/93* (2013.01); *C12Q 1/48* (2013.01); *G01N 2333/91017* (2013.01); *G01N 2333/91165* (2013.01); *G01N 2333/91171* (2013.01)

(58) Field of Classification Search
None
See application file for complete search history.

(56) References Cited

U.S. PATENT DOCUMENTS

| | | | |
|---|---|---|---|
| 8,114,650 B2 | 2/2012 | Weide et al. | |
| 2003/0108990 A1 | 6/2003 | Kamper et al. | |
| 2009/0099220 A1 | 4/2009 | Yuthavong et al. | |
| 2014/0295478 A1* | 10/2014 | Suwanakitti | C12N 9/003 435/25 |
| 2016/0230178 A1* | 8/2016 | Suwanakitti | C12N 9/003 |

FOREIGN PATENT DOCUMENTS

WO 2012/108845 A1 8/2012

OTHER PUBLICATIONS

Blum et al. (PNAS, vol. 97, No. 5, 2000, pp. 2241-2246).*
Bukhari et al. (J. of Bacteriology, vol. 105, No. 3, pp. 988-998, Mar. 1971).*
Ahrweiler et al., "Construction of a Fol Mutant Strain of *Escherichia coli* for Use in Dihydrofolate Reductase Mutagenesis Experiments", Journal of Bacteriology, vol. 170, No. 7, 1988, pp. 3301-3304.
Berglez et al., "Analysis in *Escherichia Coli* of Plasmodium falciparum Dihydropteroate Synthase (DHPS) Alleles Implicated in Resistance to Sulfadoxine", International Journal of Parasitology, vol. 34, 2004, pp. 95-100.
Bunyarataphan et al., "Evaluation of the Activities of Pyrimethamine Analogs Against Plasmodium vivax and Plasmodium falciparum Dihydrofolate Reductase-Thymidylate Synthase Using in Vitro Enzyme Inhibition and Bacterial Complementation Assays", Antimicrobial Agents and Chemotherapy, vol. 50, No. 11, 2006, pp. 3631-3637.
Chusacultanachai et al., "Novel Antifolate Resistant Mutations of Plasmodium falciparum Dihydrofolate Reductase Selected in *Escherichia coli*", Molecular and Biochemical Parasitology, vol. 120, 2002, pp. 61-72.

(Continued)

*Primary Examiner* — Hope Robinson
(74) *Attorney, Agent, or Firm* — Morrison & Foerster LLP (57) ABSTRACT

In this invention, cell lines are created for enzyme inhibitory testing of inhibitors against *Plasmodium falciparum* DHFR-TS and HPPK-DHPS. Provided the complementing DHFR-TS and HPPK-DHPS have sufficient activities to support growth of the surrogates in un-supplemented medium, the same surrogates could be used for screening inhibitors of targets against other parasite and pathogen species e.g. *Plasmodium vivax, Trypanosoma brucei, Trypanosoma cruzi, Toxoplasma gondii* or *Mycobacterium tuberculosis*. The cell lines in this invention are *Escherichia coli* strain whose thyA, folA, folK, and folP genes were disrupted using genetic knockout coupled with elimination of antibiotic resistance markers. The thyA KO, folP KO, folK KO, thyAfolA KO, folKfolP KO, thyAfolAfolP KO, thyAfolA-folK KO and thyAfolAfolKfolP KO *E. coli* cell lines are easy and convenient for testing single and combination drugs as plasmids bearing complementing parasite genes can be introduced simply by transformation using standard antibiotic selection.

15 Claims, 3 Drawing Sheets

(56) References Cited

OTHER PUBLICATIONS

Djapa et al., "Antifolate Screening Using Yeast Expressing Plasmodium vivax Dihydrofolate Reductase and in Vitro Drug Susceptibility Assay for Plasmodium falciparum", Molecular and Biochemical Parasitology, vol. 156, 2007, pp. 89-92.

Fermer et al., "Adaptation to Sulfonamide Resistance in Neisseria Meningitidis may have Required Compensatory Changes to Retain Enzyme Function: Kinetic Analysis of Dihydropteroate Synthases from N. meningitidis Expressed in a Knockout Mutant of *Escherichia coli*", Journal of Bacteriology, vol. 179, No. 3, 1997, pp. 831-837.

Ferone Robert, "Folate Metabolism in Malaria", Bulletin of the World Health Organization, vol. 55, No. 2-3, 1977, pp. 291-298.

Giladi et al., "FolM, A New Chromosomally Encoded Dihydrofolate Reductase in *Escherichia coli*", Journal of Bacteriology, vol. 185, No. 23, 2003, pp. 7015-7018.

Illarionova et al., "Biosynthesis of Tetrahydrofolate", Journal of Biological Chemistry, vol. 277. No. 32, 2002, pp. 28841-28847.

International Preliminary Report on Patentability received for PCT Patent Application No. PCT/TH2014/000045, dated Apr. 28, 2016, 6 pages.

International Search Report and Written Opinion received for PCT Patent Application No. PCT/TH2014/000045, dated Apr. 1, 2016, 7 pages.

Kumpornsin et al., "Origin of Robustness in Generating Drug-Resistant Malaria Parasites", Molecular Biology and Evolution vol. 31, No. 7, 2014, pp. 1649-1660.

Miroux et al., "Over-Production of Proteins in *Escherichia coli* Mutant Hosts that Allow Synthesis of Some Membrane Proteins and Globular Proteins at High Levels", Journal of Molecular Biology, vol. 260, 1996, pp. 289-298.

Prapunwattana et al., "Chemical Synthesis of the Plasmodium falciparum Dihydrofolate Reductase-Thymidylate Synthase Gene", Molecular and Biochemical Parasitology, vol. 83, No. 1, 1996, pp. 93-106.

Salcedo et al., "A Bifunctional Dihydrofolate Synthetase-Folylpolyglutamate Synthetase in Plasmodium falciparum Identified by Functional Complementation in Yeast and Bacteria", Molecular and Biochemical Parasitology, vol. 112, No. 2, 2001, pp. 239-252.

Sienkiewicz et al., "Chemical and Genetic Validation of Dihydrofolate Reductase-Thymidylate Synthase as a Drug Target in African Trypanosomes", Molecular Microbiology, vol. 69, No. 2, 2008, pp. 520-533.

Wooden et al., "Analysis in Yeast of Antimalaria Drugs that Target the Dihydrofolate Reductase of Plasmodium falciparum", Molecular and Biochemical Parasitology, vol. 85, No. 1, 1997, pp. 25-40.

Wu et al., "Transformation of Plasmodium falciparum Malaria Parasites by Homologous Integration of Plasmids that Confer Resistance to Pyrimethamine", Proc Natl Acad Sci. USA, vol. 93, 1996, pp. 1130-1134.

\* cited by examiner

ESCHERICHIA COLI CELL LINE WITH THYA KNOCKOUT, FOLA KNOCKOUT, AND ONE OR BOTH OF FOLP KNOCKOUT, AND FOLK KNOCKOUT

CROSS-REFERENCE TO RELATED APPLICATIONS

This is a U.S. National Phase of International Patent Application No. PCT/TH2014/000045, filed Sep. 18, 2014, which claims priority to Thai Patent Application No. 1301005569, filed Sep. 30, 2013, the contents of which are herein incorporated by reference in their entirety.

TECHNICAL FIELD

Medicinal biotechnology especially in genetically modified bacteria and dihydrofolate reductase-thymidylate synthase and 7,8-dihydro-6-hydroxymethylpterin-pyrophosphokinase-dihydropteroate synthase enzyme inhibition assay.

BACKGROUND ART

Folate cofactors, in particular members of the B vitamin complex, play an important role in cellular metabolism and growth by serving as coenzymes for the synthesis of purines and pyrimidines, the precursors of RNA and DNA. *Plasmodium* spp. and other microorganisms synthesize folate cofactors by using guanosine triphosphate (GTP) as a precursor. *Plasmodium* spp. can also salvage folate cofactors from the mammalian host. Two important enzymes in the folate biosynthesis pathway, namely dihydropteroate synthase (DHPS) and dihydrofolate reductase (DHFR), are targets of sulfa drugs (anti-DHPS) and anti-DHFR antifolates (pyrimethamine, cycloguanil, and WR99210) respectively. Species inhibited by these drugs include parasitic protozoa such as *Plasmodium falciparum, Plasmodium vivax, Toxoplasma gondii* and *Isospora belli*, and bacteria such as *Haemophilus influenzae, Escherichia coli* and *Klebsiella pneumonia*. Anti-DHPS drugs and anti-DHFR drugs are synergistic. Using both types of drugs in combination gives much enhanced efficacy, and consequently can extend the clinically effective lifetime of the drugs when compared with using either drug alone. The advantage of using combination drugs is that they can forestall the rise of drug resistance. In antifolate-resistant *Plasmodium falciparum*, a number of drug-resistance mutations have been found, including five mutations in dihydropteroate synthase and four mutations in dihydrofolate reductase. Although resistant mutations are present, the two drug targets are still valid for new drug development, with the provision that the new compounds must effectively inhibit both drug sensitive and resistant variants.

In order to evaluate antimalarial activity of compounds, in vitro antimalarial screening assay using malaria parasites grown in human red blood cells has been widely employed. However, this assay is labor intensive, expensive, and requires specialized personnel and equipment. The parasites are cultivated in red blood cells with culture media containing human serum or a suitable substitute. Routine changing of culture media and supply of new blood cells for the parasites are needed. Moreover, evaluation of drug efficacy requires microscopic, fluorescent, or radioactive methods for measuring parasite growth. These requirements are a hindrance to high throughput screening and limit antimalarial screening to laboratories with malaria culture systems in place. For target-based anti-malarial screening (which includes antifolates), surrogate models are useful alternatives when malaria culture facilities are not available. In *Plasmodium* spp., a single gene encodes a protein with DHFR and thymidylate synthase (TS) activities, making a bifunctional enzyme DHFR-TS, while in bacteria, these enzymes are encoded by separate genes, folA and thyA. Similarly, DHPS exists as a bifunctional enzyme with 7,8-dihydro-6-hydroxymethylpterin-pyrophosphokinase (HPPK) in *Plasmodium* spp. However, in bacteria, these proteins are encoded by folK and folP genes, respectively. A bacterial surrogate model screening system can be established using a cell line defective for an essential bacterial gene(s) function such that the cell can grow only in protrophic medium with the essential factor provided exogenously. The bacterial surrogate transformed with a complementary gene (e.g. homologous gene from parasite species) is able to grow in auxotrophic medium. In the presence of compounds that are inhibitory to the complementing gene, the growth of the surrogate is inhibited in auxotrophic medium. In general, growth inhibition of the bacterial surrogate correlates well with growth inhibition of the pathogenic parasite species from which the complementing gene was derived from.

Although previous bacterial surrogate models for screening compounds with parasite DHFR and DHPS inhibitory activities have been described, none has the capacity to test both types of drugs at the same time. This is because other anti-bacterial drugs are required to establish the knockout of bacterial host gene activities to make the cell dependent on parasite gene activity for growth. For bacterial surrogate models for testing anti-PfDHFR activity, endogenous bacterial DHFR was inactivated either by adding trimethoprim (chemical inhibitor of *E. coli*'s DHFR) (Bunyarataphan S., et al. 2006, Chusacultanachai S. et al. 2002), or using the PA414 strain, a folA knockout strain (Ahrweiler P. M., et al 1988, Prapunwattan P., et al 1996) or using DHFR deleted *Saccharomyces cerevisiae* mutant (Wooden J. M., et al. 1997, Djapa L. Y., et al. 2007). The anti-parasitic activities for some compounds may not correlate well with the results from the aforementioned DHFR surrogate models, since only the DHFR encoding gene is complemented. These surrogates thus do not truly model parasite DHFR function, which exists as a bifunctional enzyme with TS (see above). For DHPS surrogate models, folP deficient *E. coli*, C600 strain has been used as a bacterial surrogate model (Fermer C., et al 1997, Berglez J., et al. 2004). However, all of these bacterial surrogates have poor growth rates since they are derived from *E. coli* K strains. In some case, *E. coli* BL21(DE3) strain has been mutated to be folA and thyA deficient, but still contain antibiotic selectable markers, which are left behind as a result of the process to disrupt the bacterial gene (Sinekiewicz N., et al. 2008). Indeed, all of the above mentioned surrogate models retain antibiotic selectable markers. The retention of these markers is also disadvantageous for screening anti-parasitic drug combinations against multiple targets. This is because it not only limits introduction of multiple plasmids, or other recombinant DNA vectors carrying complementing parasite genes. For example, two different antibiotic markers would be needed to co-transform two plasmids, one with cloned parasite DHFR-TS gene complementing folA and thyA, and another one with cloned parasite HPPK-DHPS gene complementing folK and folP. The standard procedures for generating gene knockouts in *E. coli* typically employ kanamycin and/or chloramphenicol resistance markers, which are also commonly-used markers for transformation vectors. Whilst it is facile to transform say, a surrogate cell harboring a single kanamycin resistance marker with a plasmid bearing a beta-lactamase marker, it becomes increasingly difficult to find suitable antibiotic resistance markers for plasmid transformation as the number of genes knocked out in the surrogate increases. Unless a strategy is employed to remove resistance markers, no suitable markers would be available for selection of cells transformed with complementing genes as the surrogate would already be resistant to multiple different antibiotics. For this reason, there is currently no surrogate screening system for testing combination drugs against DHFR-TS and HPPK-DHPS. Drug combinations against these targets are important, as they have been proven to be effective anti-parasitic chemotherapies which is used to treat malaria.

In the subject invention, a model is described for testing combination drugs which inhibit both parasite DHFR-TS and HPPK-DHPS enzyme activities. This invention entails an *Escherichia coli* strain whose thyA, folA, folK and folP genes were sequentially disrupted using genetic knockout coupled with elimination of antibiotic resistance markers. We evaluated the use of this invention as a host for screening inhibitors against DHFR and/or DHPS of *Plasmodium* or other apicomplexan parasites. The tools, thyAfolA knockout (KO), folKfolP KO and thyAfolAfolKfolP KO *E. coli* are easy and convenient for testing single and combination drugs as plasmids bearing complementing parasite genes can be introduced simply by transformation. The assay results using this model are consistent with those from the conventional antimalarial screening method using malaria parasite. With this tool, it is feasible to perform antifolate screening against malaria and other parasitic disease in a laboratory with facilities for bacteria cell culture, which more are widely available than parasite culture facilities.

DISCLOSURE OF INVENTION

The purpose of this invention is to create a bacterial model suitable for antifolate screening, both for single drugs and drugs in combination inhibiting up to four enzyme targets in the folate biosynthyesis pathway. The invention involves thyA (thymidylate synthase), and/or folA (dihydroiolatereducatse), and/or folP (dihydropteroate synthase), and/or folK (7,8-dihydro-6-hydroxymethylpterin-pyrophosphokinase) in *Escherichia coli* BL21 (DE3).

1. Construction of a Marker-free Single thyA KO, folA KO, folP KO, or folK KO or Multiple Gene Knockout *E. coli* Strains 1.1 Construction of a marker-free single thyA KO, folA KO, folP KO, or folK KO *E. coli* Each single knockout *E. coli* was constructed in four steps:

1.1.1 Transformation of pKD46 Plasmid into *Escherichia coli* BL21(DE3) Using Heat Shock Method

*Escherichia coli* BL21(DE3) was transformed with pKD46 plasmid for expressing Red recombinase, an enzyme that can promote homologous recombination. Following transformation, the bacteria harboring the pKD46 plasmid were cultured at 30 degrees Celsius since the plasmid contains temperature-sensitive origin of replication.

1.1.2 Construction of Plasmids Used for Disrupting Target Genes

Plasmids containing regions homologous to 5' and 3' sequences of thyA, folA, folP, or folK genes for gene targeting were created with an insertion of an antibiotic resistance gene either kanamycin resistance gene (KmR) or chloramphenicol resistance gene (CmR) between the 5' and 3' targeting sequences. Each gene-targeting DNA fragment was then amplified by PCR as a linear DNA fragment for homologous recombination.

1.1.3 Introduction of Linear Targeting DNA into *E. coli* BL21(DE3) by Electroporation Following electroporation, the gene-targeting DNA fragment containing an antibiotic resistant gene was introduced to the *Escherichia coli* BL21(DE3) harboring pKD46. Upon Red recombinase assisted recombination, the single knockout *E. coli* can be selected on LB plate supplemented with appropriate antibiotic (kanamycin or chloramphenicol), thymidine, and folinic acid at 37 degrees Celsius. Since pKD46 cannot replicate at 37 degree Celsius, it will be lost. The resulting *E. coli* are called "single thyA, folA, folP, or folK knockout *E. coli* with antibiotic resistant marker" or in general "single knockout *E. coli* with antibiotic resistant marker"

1.1.4 Eliminate Antibiotic Resistance Gene

The pCP20 plasmid for expressing FLP recombinase was transformed into the single KO *E. coli* with antibiotic resistant marker by the heat shock method. Cells were cultured in LB supplemented with thymidine and folinic acid at 30 degrees Celsius for 3 hours to allow FLP recombinase enzyme to express and remove the antibiotic resistance gene. The cells were then cultured at 37 degrees Celsius for 1 hour to allow the loss of the pCP20 plasmid. The resulting cell is called "marker-free single gene KO *E. coli*". Marker-free thyA KO, folA KO, folP KO, or folK KO *E. coli* strains were verified to have lost genes of interest and antibiotic resistance gene by PCR.

1.2 Construction of Marker-free Double Knockout *E. coli* (thyAfolA KO and folPfolK KO *E. coli*).

Marker-free single knockout *E. coli* strains from step 1.1 were used as parental strains for subsequent gene knockout instead of wild type BL21(DE3). Methods described in section 1.1.1 to 1.1.4 were used to construct the marker-free double knockout *E. coli* strains.

1.3 Construction of marker-free triple knockout *E. coli* (thyAfolAfolP KO and thyAfolAfolK KO)

Marker-free double knockout *E. coli* strains from step 1.2 were used as parental strains. Methods described in section 1.1.1 to 1.1.4 were used to construct the marker-free triple knockout *E. coli* strains.

1.4 Construction of Marker-Free Quadruple Knockout *E. coli* (thyAfolAfolPfolK KO).

Marker-free triple knockout *E. coli* strains from step 1.3 were used as a parental strain. Methods as described in section 1.1.1 to 1.1.4 were used to construct the marker-free quadruple knockout *E. coli*.

As described above, *E. coli* BL21(DE3) thyAfolAfolPfolK KO, *E. coli* BL21(DE3) thyAfolAfolP KO, *E. coli* BL21(DE3) thyAfolAfolK KO, *E. coli* BL21(DE3) thyAfolA KO, *E. coli* BL21(DE3) folPfolK KO, *E. coli* BL21 (DE3) thyA KO, *E. coli* BL21(DE3) folP KO, and *E. coli* BL21(DE3) folK KO were constructed using this method. These strains are referred to hereafter as PEcΔTFPK, PEcΔTFP, PEcΔTFK, PEcΔTF, PEcΔPK, PEcΔT, PEcΔP and PEcΔK, respectively.

Example 1

Construction of a Triple thyAfolAfolP Knockout *E. coli* (PEcΔTFP)

There are 4 steps to create a triple thyAfolAfolP KO *E. coli* BL21(DE3), referred to hereafter as PEcΔTFP.

1. Transform the double mutant PEcΔTF with pKD46 plasmid for expressing Red recombinase enzyme by the heat shock method. Following transformation, the cells were cultured at 30 degree Celsius.

Figure 1A:
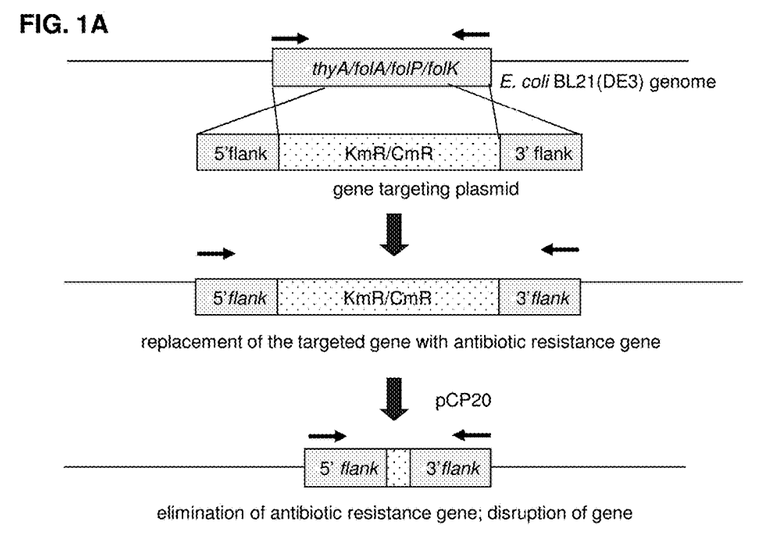
FIG. 1A: Invention step for creating a knockout gene (thyA KO or folA KO or folP KO or folK KO) in *E. coli* by a double crossover strategy.

2. Construct a folP targeting plasmid containing kanamycin (KmR) resistance gene flanked by 5' and 3' homologous sequences of folP gene (FIG. 1a) and PCR amplification as linear folP targeting DNA fragment.

3. Introduce the linear folP targeting DNA fragment to the double mutant PEcΔTF harboring pKD46 plasmid by electroporation.

In this step Red recombinase enzyme encoded on pKD46 will help DNA recombination between linear folP targeting DNA and homologous genomic DNA of the double mutant (PEcΔTF). Cells were then selected on LB agar containing kanamycin, thymidine, and folinic acid. This cell is called a triple mutant thyAfolAfolP KO *E. coli* BL21(DE3) with kanamycin resistance marker, or referred to hereafter as PEcΔTFP-KmR.

4. Transform PEcΔTFP-KmR with pCP20 plasmid harboring FLP recombinase gene by heat shock method to eliminate the kanamycin resistance marker. Following transformation, the cells were cultured at 30 degrees Celsius for 3 hours to permit expression of FLP recombinase enzyme for elimination of KmR marker, and then at 37 degrees Celsius for 1 hour in LB supplemented with thymidine and folinic acid to eliminate pCP20 plasmid. This cell is called a marker-free triple mutant thyAfolAfolP KO *E. coli* BL21 (DE3), referred to hereafter as PEcΔTFP.

Figure 1B:
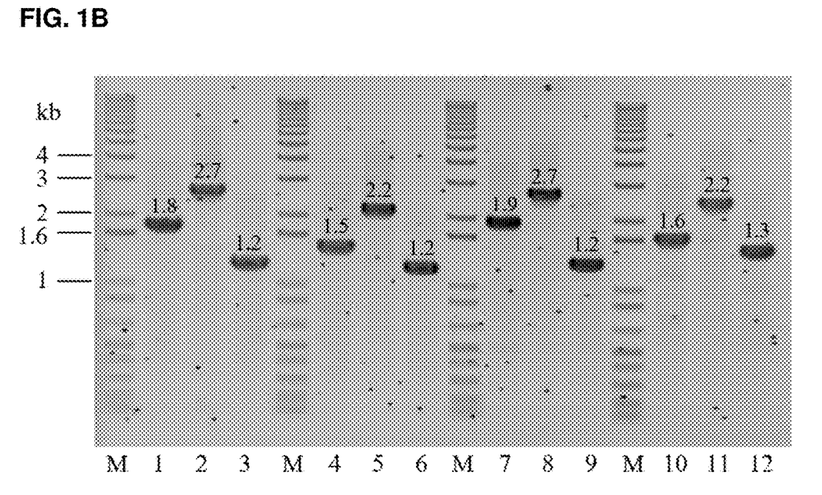
FIG. 1B: PCR results for verification of gene knockouts in *E. coli*.

The triple knockout strains, PEcΔTFP-KmR and PEcΔTFP, were verified by PCR. PCR products from knockout strains were compared with wild-type *E. coli* BL21(DE3). The expected sizes of PCR products are shown in FIG. 1b. Lanes 1-3 show PCR product of wild type thyA gene, and thyA KO gene with. KmR, and marker-free thyA KO gene with the expected size of 1.8, 2.7, and 1.2 kb, respectively. Lanes 4-6 show PCR product of wild type folA gene, and folA KO gene with CmR, and marker-free folA KO gene with the expected size of 1.5, 2.2, and 1.2 kb, respectively. Lanes 7-9 show PCR product of wild type folP gene, and folP KO gene with KmR, and marker-free folP KO gene with the expected size of 1.9, 2.7, and 1.2 kb, respectively. The size of the PCR products of the invented cells were as expected suggesting a success in gene disruption and antibiotic resistance marker removal. Therefore, the triple mutant cell PEcΔTFP was obtained.

Example 2

Construction of a Triple thyAfolAfolK Knockout (PEcΔTFK)

There are 4 steps to create a triple thyAfolAfolK KO *E. coli* BL21(DE3), referred to hereafter as PEcΔTFK.

1. Transform the double mutant (PEcΔTF) with pKD46 plasmid for expressing Red recombinase enzyme by heat shock method. Following transformation, the cells were cultured in 30 degree Celsius.

2. Construct afolK targeting plasmid containing chloramphenicol (CmR) resistance gene flanked by 5' and 3' homologous sequences of folK gene and PCR amplification as linear folK targeting DNA fragment.

3. Introduce the linear folK targeting fragment to the double mutant PEcΔTF harboring pKD46 plasmid by electroporation.

In this step Red recombinase enzyme encoded on pKD46 will help DNA recombination between linear folK targeting plasmid and homologous genomic DNA of the double mutant PEcΔTF. Cells were then selected on LB agar containing chloramphenicol, thymidine, and folinic acid. This cell is called a triple mutant thyAfolAfolK KO *E. coli* BL21(DE3) with chloramphenicol resistance marker, or referred to hereafter as PEcΔTFK-CmR.

4. Transform PEcΔTFK-CmR with pCP20 plasmid harboring FLP recombinase gene by heat shock method to eliminate the chloramphenicol resistance marker. Following transformation, the cells were cultured at 30 degrees Celsius for 3 hours to permit expression of FLP recombinase enzyme for elimination of CmR marker, and then at 37 degrees Celsius for 1 hour in LB supplemented with thymidine and folinic acid to eliminate pCP20 plasmid. This cell is called a marker-free triple mutant thyAfolAfolK KO *E. coli* BL21(DE3), referred to hereafter as PEcΔTFK.

The triple knockout strains, PEcΔTFK-CmR and PEcΔTFK, were verified by PCR. PCR products from knockout strains were compared with wild-type *E. coli* BL21(DE3). The expected sizes of PCR products are shown in FIG. 1b. Lanes 1-3 show PCR product of wild type thyA gene, and thyA KO gene with KmR, and marker-free thyA KO gene with the expected size of 1.8, 2.7, and 1.2 kb, respectively. Lanes 4-6 show PCR product of wild type folA gene, and folA KO gene with CmR, and marker-free folA KO gene with the expected size of 1.5, 2.2, and 1.2 kb, respectively. Lanes 10-12 show PCR product of wild type folK gene, and folK gene with CmR, and marker-free folK gene with the expected size of 1.6, 2.2, and 1.3 kb, respectively. The size of the PCR products of the invented cells were as expected suggesting a success in gene disruption and antibiotic resistance marker removal.

Therefore, the triple mutant cell PEcΔTFK was obtained.

Example 3

Construction of a Quadruple thyAfolAfolPfolk Knockout (PEcΔTFPK)

There are 4 steps to create a quadruple thyAfolAfolPfolK KO *E. coli* BL21(DE3), referred to hereafter as PEcΔTFPK.

1. Transform a triple mutant PEcΔTFP with pKD46 plasmid for expressing Red recombinase enzyme by heat shock method. Following transformation, the cells were cultured at 30 degrees Celsius.

2. Construct afolK targeting plasmid containing chloramphenicol (CmR) resistance gene flanked by 5' and 3' homologous sequences of folK gene and PCR amplification as linearfolK targeting DNA fragment.

3. Introduce the linearfolK targeting fragment to the triple mutant PEcΔTFP harboring pKD46 plasmid by electroporation.

In this step Red recombinase enzyme encoded on pKD46 will help DNA recombination between linear folK targeting plasmid and homologous genomic DNA of the triple mutant PEcΔTFP. Cells were then selected on LB agar containing chloramphenicol, thymidine, and folinic acid. This cell is called a quadruple mutant thyAfolAfolPfolK KO *E. coli* BL21(DE3) with chloramphenicol resistance marker, or referred to hereafter as PEcΔTFPK-CmR.

4. Transform PEcΔTFPK-CmR with pCP20 plasmid harboring FLP recombinase gene by heat shock method to eliminate the chloramphenicol resistance marker. Following transformation, the cells were cultured at 30 degrees Celsius for 3 hours to permit expression of FLP recombinase enzyme for elimination of CmR marker, and then at 37 degrees Celsius for 1 hour in LB supplemented with thymidine and folinic acid to eliminate pCP20 plasmid. This cell is called a marker-free quadruple mutant thyAfolAfolPfolK KO *E. coli* BL21(DE3), referred to hereafter as PEcΔTFPK.

The quadruple knockout strains, PEcΔTFPK-CmR and PEcΔTFPK, were verified by PCR. The PCR products from knockout strains were compared with wild-type *E. coli* BL21(DE3) as shown in FIG. 1*b*. Lanes 1-3 show PCR product of wild type thyA gene, and thyA KO gene with KmR, and marker-free thyA KO gene with the expected size of 1.8, 2.7, and 1.2 kb, respectively. Lanes 4-6 show PCR product of wild type folA gene, and folA KO gene with CmR, and marker-free folA KO gene with the expected size of 1.5, 2.2, and 1.2 kb, respectively. Lanes 7-9 show PCR product of wild type folP gene, and folP KO gene with KmR, and marker-free folP KO gene with the expected size of 1.9, 2.7, and 1.2 kb, respectively. Lanes 10-12 show PCR product of wild type folK gene, and folK gene with CmR, and marker-free folK gene with the expected size of 1.6, 2.2, and 1.3 kb, respectively. The size of the PCR products of the invented cells were as expected suggesting a success in gene disruption and antibiotic resistance marker removal.

Therefore, the quadruple mutant cell PEcΔTFPK was obtained.

2. Complementation Assay of PEcΔTFPK Surrogate Host

Figure 2A:
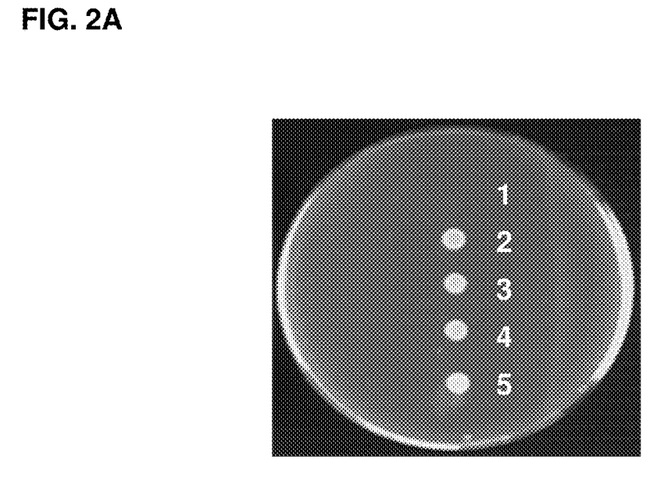
FIG. 2A: Assay of a quadruple mutant PEcΔTFPK without any plasmid (spot 1) and with plasmids containing Pfdhfr-ts (WT) and Pfhppk-dhps (WT) (spots 2-5).
Figure 2B:
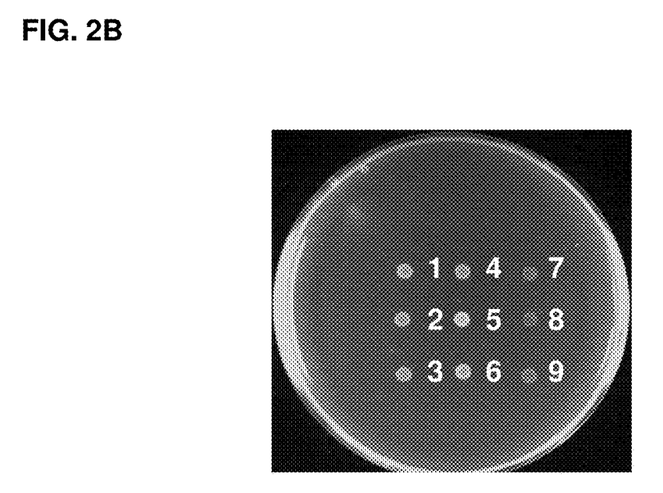
FIG. 2B: Assay of a quadruple mutant PEcΔTFPK with plasmids containing variants of Pfdhfr-ts and Pfhppk-dhps.

The function of a quadruple mutant PEcΔTFPK as a surrogate host for drug screening system was tested by complementation assay, to see if the cell can be rescued by plasmids expressing heterologous dhfr-ts and hppk-dhps genes. PEcΔTFPK cells with and without plasmids containing wild type and mutant dhfr-ts and hppk-dhps genes from *Plasmodium falciparum* were grown on M9CA minimal agar with ampicillin, chloramphenicol (the markers of dhfr-ts and hppk-dhps expressing plasmids, respectively) and L-arabinose (an inducer for gene expression). FIG. 2*a* shows growth capability of PEcΔTFPK cells, with and without heterologous genes, on auxotrophic medium lacking thymidine and folinic acid. PEcΔTFPK (spot 1) surrogate host could not grow, while 4 colonies of PEcΔTFPK expressing wild type Pfdhfr-ts and Pfhppk-dhps (spots 2-5) can grow on the same un-supplemented medium. Furthermore, variants of Pfdhfr-ts and Pfhppk-dhps can also complement surrogate cells in minimal media with L-arabinose as shown in FIG. 2*b*.

The growth rates of PEcΔTFPK transformed with different Pfdhfr-ts and Pfhppk-dhps variants have also been examined. The cells were cultured in minimal media with L-arabinose as an inducer and appropriate antibiotic in 96 wells plate at 37 degrees Celsius in an incubator shaker at 1000 rpm. Cell growth was measured as the spectrophotometer optical density at 600 nm every hour for 9 hours. As shown in Table 1, all variants can support growth to varying extents. DHFR-TS and HPPK-DHPS from the same parasite strains can support better bacterial growth rate than those with strain-mismatching of both enzymes. These suggest the different catalytic activity of these variants and that balance activity of DHFR-TS and HPPK-DHPS has been fixed by the nature for these variants.

From these results, the PEcΔTFPK can be used as a surrogate host system for testing enzyme fitness of *Plasmodium falciparum* DHFR-TS and HPPK-DHPS targets, including wildtype and variants. The same surrogate could therefore also be used to screen inhibitors against other parasite and pathogenic species, e.g. *Plasmodium vivax, Trypanosoma brucei, Trypanosoma cruzi, Toxoplasma gondii* or *Mycobacterium tuberculosis*, provided that the complementing gene(s) possess sufficient activity to complement growth of PEcΔTFPK.

3. Use Mutant *E. coli* BL21(DE3) as a Host for Antifolate Drug Screening

Figure 3A:
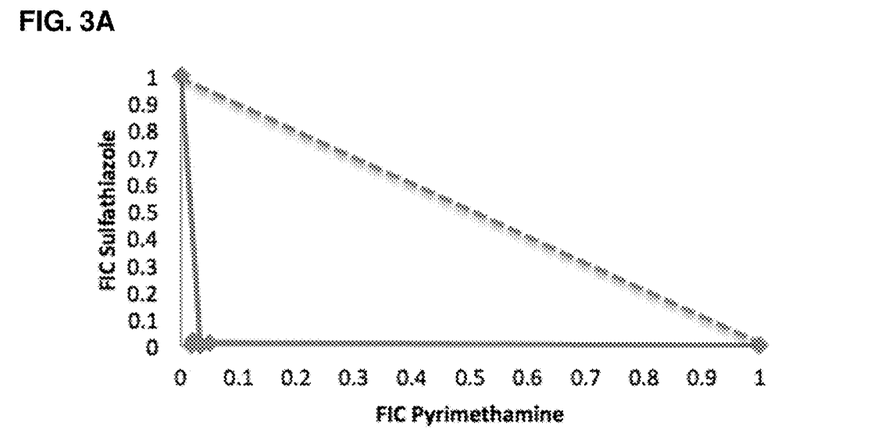
Figure 3B:
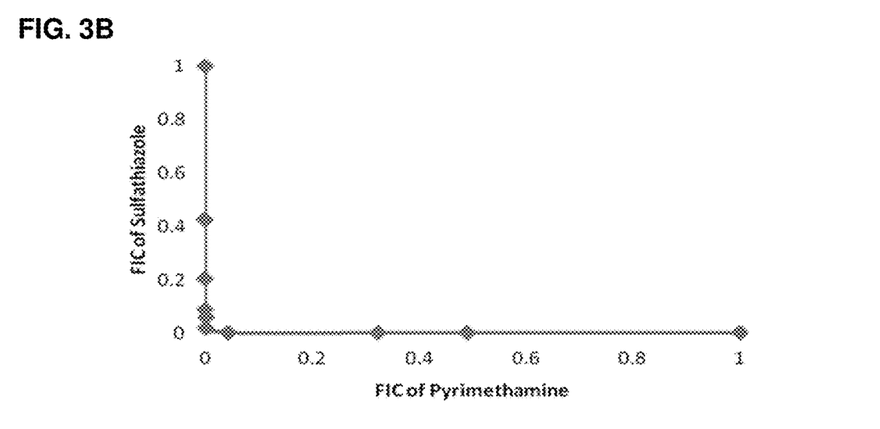

Pyrimethamine and sulfathiazole were chosen for this experiment. The 50% inhibitory concentrations ($IC_{50}$) of each drug were calculated from dose-response growth curves for PEcΔTFP and PEcΔTFPK surrogates transformed with plasmids containing wild type Pfdhfr-ts and Pfhppk-dhps. Cells were incubated in various concentrations of drug in minimal media supplemented with L-arabinose as an inducer and antibiotics for selection of complementing plasmids in 96-well plates at 37 degrees Celsius for 16 hours. The measured $IC_{50}$ values of pyrimethamine and sulfathiazole from surrogate host systems are very similar to values from the standard hypoxanthine incorporation method in *Plasmodium falciparum* parasites (0.041±0.006 and 135.45±0.49 μM respectively). PEcΔTFP transformed with plasmids containing Pfdhfr-ts (WT) and Pfhppk-dhps (WT) and PEcΔTFPK transformed with plasmids containing Pfdhfr-ts (WT) and Pfhppk-dhps (WT) were tested with the combination of pyrimethamine and sulfathiazole drugs. Isobologram analysis of the $IC_{50}$ values reveal synergism in both surrogates, as expected for this combination (FIG. 3).

From these results show PEcΔTFP and PEcΔTFPK can be used as surrogate host systems for enzyme inhibitory testing of inhibitors against *Plasmodium falciparum* DHFR-TS and HPPK-DHPS. Provided the complementing DHFR-TS and HPPK-DHPS have sufficient activities to support growth of the surrogates in un-supplemented medium (see above), the same surrogates could be used for screening inhibitors of targets against other parasite and pathogen species e.g. *Plasmodium vivax, Trypanosoma brucei, Trypanosoma cruzi, Toxoplasma gondii* or *Mycobacterium tuberculosis*.

BRIEF DESCRIPTION OF DRAWINGS

FIG. 2A-B: Complementation assay of dihydrofolate reductase-thymidylate synthase and 7,8-dihydro-6-hydroxymethylpterin-pyrophosphokinase-dihydropteroate synthase enzyme in invention.

Spot 1: PEcΔTFPK (WT/WT), A quadruple thyAfolAfolPfolK KO *E. coli* BL21(DE3) with plasmids for expressing Pfdhfr-ts (WT) and Pfhppk-dhps (WT)

Spot 2: PEcΔTFPK (WT/K1), A quadruple thyAfolAfolPfolK KO *E. coli* BL21(DE3) with plasmids for expressing Pfdhfr-ts (WT) and Pfhppk-dhps (A437G+A581G, K1)

Spot 3: PEcΔTFPK (WT/V1S), A quadruple thyAfolAfolPfolK KO *E. coli* BL21(DE3) with plasmids for expressing Pfdhfr-ts (WT) and Pfhppk-dhps (S436F+A437G+A613T, V1S)

Spot 4: PEcΔTFPK (K1/WT), A quadruple thyAfolAfolPfolK KO *E. coli* BL21(DE3) with plasmids for expressing Pfdhfr-ts (C59R+S108N, K1) and Pfhppk-dhps (WT)

Spot 5: PEcΔTFPK (K1/K1), A quadruple thyAfolAfolPfolK KO *E. coli* BL21(DE3) with plasmids for expressing Pfdhfr-ts (C59R+S108N, K1) and Pfhppk-dhps (A437G+A581G, K1)

Spot 6: PEcΔTFPK (K1/V1S), A quadruple thyAfolAfolPfolK KO *E. coli* BL21(DE3) with plasmids for expressing Pfdhfr-ts (C59R+S108N, K1) and Pfhppk-dhps (S436F+A437G+A613T, V1S)

Spot 7: PEcΔTFPK (V1S/WT), A quadruple thyAfolAfolPfolK KO *E. coli* BL21(DE3) with plasmids for expressing Pfdhfr-ts (N51I+C59R+S108N+I164L, V1S) and Pfhppk-dhps (WT)

Spot 8: PEcΔTFPK (V1S/K1), A quadruple thyAfolAfolPfolK KO *E. coli* BL21(DE3) with plasmids for expressing Pfdhfr-ts (N51I+C59R+S108N+I164L, V1S) and Pfhppk-dhps (A437G+A581G, K1)

Spot 9: PEcΔTFPK (V1S/V1S), A quadruple thyAfolAfolPfolK KO *E. coli* BL21(DE3) with plasmids for expressing Pfdhfr-ts (N51I+C59R+S108N+I164L, V1S) and Pfhppk-dhps (S436F+A437G+A613T, V1S)

FIG. 3A-B: Isobologram of pyrimethamine and sulfathiazole against the invented host carrying plasmids for expressing Pfdhfr-ts (WT) and Pfhppk-dhps (WT). Synergistic effect was observed from both invented host, a triple mutant, PEcΔTFP (FIG. 3A) and a quadruple mutant, PEcΔTFPK (FIG. 3B).

Table 1 Growth rate of quadruple mutant PEcΔTFPK expressing different Pfdhfr-ts and Pfhppk-dhps variants in comparison with *E. coli* BL21(DE3) in minimal media with L-arabinose.

PEcΔTFPK (WT/WT): A quadruple thyAfolAfolPfolK KO *E. coli* BL21(DE3) with plasmids for expressing Pfdhfr-ts (WT) and Pfhppk-dhps (WT)

PEcΔTFPK (WT/K1): A quadruple thyAfolAfolPfolK KO *E. coli* BL21(DE3) with plasmids for expressing Pfdhfr-ts (WT) and Pfhppk-dhps (A437G+A581G, K1)

PEcΔTFPK (WT/V1S): A quadruple thyAfolAfolPfolK KO *E. coli* BL21(DE3) with plasmids for expressing Pfdhfr-ts (WT) and Pfhppk-dhps (S436F+A437G+A613T, V1S)

PEcΔTFPK (K1/WT): A quadruple thyAfolAfolPfolK KO *E. coli* BL21(DE3) with plasmids for expressing Pfdhfr-ts (C59R+S108N, K1) and Pfhppk-dhps (WT)

PEcΔTFPK (K1/K1): A quadruple thyAfolAfolPfolK KO *E. coli* BL21(DE3) with plasmids for expressing Pfdhfr-ts (C59R+S108N, K1) and Pfhppk-dhps (A437G+A581G, K1)

PEcΔTFPK (K1/V1S): A quadruple thyAfolAfolPfolK KO *E. coli* BL21(DE3) with plasmids for expressing Pfdhfr-ts (C59R+S108N, K1) and Pfhppk-dhps (S436F+A437G+A613T, V1S)

PEcΔTFPK (V1S/WT): A quadruple thyAfolAfolPfolK KO *E. coli* BL21(DE3) with plasmids for expressing Pfdhfr-ts (N51I+C59R+S108N+I164L, V1S) and Pfhppk-dhps (WT)

PEcΔTFPK (V1S/K1): A quadruple thyAfolAfolPfolK KO *E. coli* BL21(DE3) with plasmids for expressing Pfdhfr-ts (N51I+C59R+S108N+I164L, V1S) and Pfhppk-dhps (A437G+A581G, K1)

PEcΔTFPK (V1S/V1S): A quadruple thyAfolAfolPfolK KO *E. coli* BL21(DE3) with plasmids for expressing Pfdhfr-ts (N51I+C59R+S108N+I164L, V1S) and Pfhppk-dhps (S436F+A437G+A613T, V1S)

| Cell | dhfr-ts* | hppk-dhps** | % growth of cell*** | Fitness of dhps mutant (under same dhfr background shown in the parenthesis)[$] | Fitness of dhfr mutant (under same dhps background shown in the parenthesis)[#] |
|---|---|---|---|---|---|
| BL21(DE3) | thyA + folA | folK + folP | 100 ± 0.00 | — | — |
| PEcΔTFPK(WT/WT) | WT | WT | 74.94 ± 0.90 | 1.00 (WT-dhfr) | 1.00 (WT-dhps) |
| PEcΔTFPK(WT/K1) | WT | K1 | 89.23 ± 1.15 | 1.19 (WT-dhfr) | 1.00 (K1-dhps) |
| PEcΔTFPK(WT/V1S) | WT | V1S | 59.60 ± 0.85 | 0.79 (WT-dhfr) | 1.00 (V1S-dhps) |
| PEcΔTFPK(K1/WT) | K1 | WT | 71.57 ± 1.73 | 1.00 (K1-dhfr) | 0.95 (WT-dhps) |
| PEcΔTFPK(K1/K1) | K1 | K1 | 77.32 ± 2.08 | 1.08 (K1-dhfr) | 0.87 (K1-dhps) |
| PEcΔTFPK(K1/V1S) | K1 | V1S | 77.00 ± 1.07 | 1.08 (K1-dhfr) | 1.29 (V1S-dhps) |
| PEcΔTFPK(V1S/WT) | V1S | WT | 67.85 ± 1.35 | 1.00 (V1S-dhfr) | 0.90 (WT-dhps) |
| PEcΔTFPK(V1S/K1) | V1S | K1 | 63.47 ± 0.74 | 0.93 (V1S-dhfr) | 0.71 (K1-dhps) |
| PEcΔTFPK(V1S/V1S) | V1S | V1S | 78.05 ± 0.74 | 1.15 (V1S-dhfr) | 1.31 (V1S-dhps) |

*mutation at C59R + S108N (K1) and N51I + C59R + S108N + I164L (V1S) of PfDHFR
**mutation at A437G + A581G (K1) and S436F + A437G + A613T (V1S) of PfDHPS
***values are mean growth relative to untreated control (100%) ± standard deviation

[$]ratio of growth rate of PEcΔTFPK expressing dhps mutant and that expressing WT dhps under the same dhfr type

[#]ratio of growth rate of PEcΔTFPK expressing dhfr mutant and that expressing WT dhfr under the same dhps type

BEST MODE FOR CARRYING OUT THE INVENTION

As described above in disclosure of invention section

INDUSTRIAL APPLICABILITY

As described above in disclosure of invention section

REFERENCES

1. Bunyarataphan S., Leartsakulpanich U., Taweechai S., Tarnchompoo B., Kamchonwongpaisan S., and Yuthavong Y. (2006) Evaluation of the Activities of Pyrimethamine Analogs against *Plasmodium vivax* and *Plasmodium falciparum* Dihydrofolate Reductase-Thymidylate Synthase Using In Vitro Enzyme Inhibition and Bacterial Complementation Assay. *Antimicrobial Agents and Chemotherapy* 50: 3631-3637.
2. Chusacultanachai S., Thiensathit P., Tarmchompoo B., Sirawaraporn W., and Yuthavong Y. (2002) Novel antifolate resistant mutations of *Plasmodium falciparum* dihydrofolate reductase selected in *Escherichia coli. Molecular and Biochemical Parasitology* 120: 61-72.

3. Ahrweiler P. M., and Frieden C. (1988) Construction of afol Mutant Strain of *Escherichia coli* for Use in Dihydrofolate Reductase Mutagenesis Experiments. *Journal of Bacteriology* 170: 3301-3304.
4. Prapunwattana P., Sirawaraporn W., Yuthavong Y., and Santi D. V. (1996) Chemical synthesis of the *Plasmodium falciparum* dihydrofolate reductase-thymidylate synthase gene. *Molecular and Biochemical Parasitology* 83: 93-106.
5. Wooden J. M., Hartwell L. H., Vasquez B., and Sibley C. H. (1997) Analysis in yeast of antimalaria drugs that target the dihydrofolate reductase of *Plasmodium falciparum*. *Molecular and Biochemical Parasitology* 85: 25-40.
6. Djapa L. Y., Basco L. K., Zelikson R., Rosowsky A., Djman J. A., Yonkeu J. N., Fukuhara M. B., and Mazabraud A. (2007) Antifolate screening using yeast expressing *Plasmodium vivax* dihydrofolate reductase and in vitro drug susceptibility assay for *Plasmodium falciparum*. *Molecular and Biochemical Parasitology* 156: 89-92.
7. Fermer C., and Swedberg G. (1997) Adaptation to Sulfonamide Resistance in *Neisseria meningitides* May Have Required Compensatory Changes to Retain Enzyme Function: Kinetic Analysis of Dihydropteroate Synthases from *N. meningitides* Expressed in a Knockout Mutant of *Escherichia coli*. *Journal of Bacteriology* 179: 831-837.
8. Berglez J., Iliades P., Sirawaraporn W., Coloe P., and Macreadie I. (2004) Analysis in *Escherichia coli* of *Plasmodium falciparum* dihydropteroate synthase (DHPS) alleles implicated in resistance to sulfadoxine. *International Journal for Parasitology* 34: 95-100.
9. Sienkiewicz N., Jaroslawski S., Wyllie S., and Fairlamb A. H. (2008) Chemical and genetic validation of dihydrofolate reductase—thymidylate synthase as a drug target in African trypanosomes. *Molecular Microbiology* 69: 520-533.

The invention claimed is:
1. An *Escherichia coli* (*E. coli*) cell line in which its thymidylate synthase (thyA), dihydrofolate reductase (folA), and one or both of its dihydropteroate synthase (folP) and 7,8-dihydro-6-hydroxymethylpterin-pyrophosphokinase (folK) genes have been disrupted by genetic knockout, and wherein antibiotic resistance genes used to create the genetic knockout have been functionally eliminated.
2. The cell line of claim 1, wherein the cell line is *E. coli* type BL21(DE3).
3. The cell line of claim 1, wherein cells of the cell line comprise one or both of a parasite dihydrofolate reductase-thymidylate synthase (DHFR-TS) gene for expression of a parasite DHFR-TS enzyme, and a parasite 7,8-dihydro-6-hydroxymethylpterin-pyrophosphokinase-dihydropteroate synthase (HPPK-DHPS) gene for expression of a parasite HPPK-DHPS enzyme.
4. The cell line of claim 3, wherein one or both of the parasite DHFR-TS gene and the parasite HPPK-DHPS gene are of a parasite selected from the group consisting of *Plasmodium falciparum*, *Plasmodium vivax*, *Trypanosoma brucei*, *Trypanosoma cruzi*, *Toxoplasma gondii*, and *Mycobacterium tuberculosis*.
5. The cell line of claim 3, wherein one or both of the parasite DHFR-TS gene and the parasite HPPK-DHPS gene are present on plasmids.
6. The cell line of claim 5 wherein the cells comprise the parasite DHFR-TS gene.
7. The cell line of claim 5, wherein the cells comprise the parasite HPPK-DHPS gene.
8. The cell line of claim 5, wherein the cells comprise the parasite DHFR-TS gene and the parasite HPPK-DHPS gene.
9. The cell line of claim 8, wherein the heterologous expression of the parasite DHFR-TS enzyme and the parasite HPPK-DHPS enzyme permits the cells to grow on minimal media without thymidine and folinic acid supplementation.
10. The cell line of claim 1, wherein cells of the cell line are sensitive to one or both of ampicillin and chloramphenicol.
11. The cell line of claim 1, wherein the thyA, folA, folP and folK genes have been disrupted by genetic knockout (*E. coli* thyAfolAfolPfolK KO).
12. The cell line of claim 1, wherein the thyA, folA and folP genes have been disrupted by genetic knockout (*E. coli* thyAfolAfolP KO).
13. The cell line of claim 1, wherein the thyA, folA and folK genes have been disrupted by genetic knockout (*E. coli* thyAfolAfolK KO).
14. A method of identifying an inhibitor of a parasite DHFR-TS enzyme or a parasite HPPK-DHPS enzyme, comprising:
   a) growing the *E. coli* cell line of claim 8 in the presence and absence of a candidate drug in media; and
   b) identifying the candidate drug as an inhibitor of the parasite DHFR-TS enzyme or the parasite HPPK-DHPS enzyme when the cell line grows more quickly in the absence as compared to the presence of the candidate drug.
15. The method of claim 14, wherein the media does not comprise a thymidine supplement and a folinic acid supplement.

* * * * *